United States Patent
Gattone et al.

(10) Patent No.: US 10,335,414 B2
(45) Date of Patent: Jul. 2, 2019

(54) USE OF TRPV4 ANTAGONISTS TO AMELIORATE HYDROCEPHALUS AND RELATED MATERIALS AND METHODS

(71) Applicant: Indiana University Research and Technology Corporation, Indianapolis, IN (US)

(72) Inventors: Vincent Gattone; Bonnie Blazer-Yost, Indianapolis, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 635 days.

(21) Appl. No.: 14/647,387

(22) PCT Filed: Dec. 3, 2013

(86) PCT No.: PCT/US2013/072758
§ 371 (c)(1),
(2) Date: May 26, 2015

(87) PCT Pub. No.: WO2014/089013
PCT Pub. Date: Jun. 12, 2014

(65) Prior Publication Data
US 2015/0290206 A1    Oct. 15, 2015

Related U.S. Application Data

(60) Provisional application No. 61/872,048, filed on Aug. 30, 2013, provisional application No. 61/732,708, filed on Dec. 3, 2012.

(51) Int. Cl.
| | | |
|---|---|---|
| *A61K 31/00* | (2006.01) |
| *A61K 31/18* | (2006.01) |
| *A61M 27/00* | (2006.01) |
| *A61K 31/165* | (2006.01) |
| *A61K 31/4439* | (2006.01) |
| *A61K 31/28* | (2006.01) |
| *A61K 31/55* | (2006.01) |
| *A61K 31/202* | (2006.01) |
| *A61K 31/225* | (2006.01) |
| *A61K 31/405* | (2006.01) |
| *A61K 31/495* | (2006.01) |
| *A61K 31/496* | (2006.01) |
| *A61K 31/5377* | (2006.01) |
| *A61K 31/4995* | (2006.01) |

(52) U.S. Cl.
CPC .......... *A61K 31/5377* (2013.01); *A61K 31/00* (2013.01); *A61K 31/165* (2013.01); *A61K 31/18* (2013.01); *A61K 31/202* (2013.01); *A61K 31/225* (2013.01); *A61K 31/28* (2013.01); *A61K 31/405* (2013.01); *A61K 31/4439* (2013.01); *A61K 31/495* (2013.01); *A61K 31/496* (2013.01); *A61K 31/4995* (2013.01); *A61K 31/55* (2013.01); *A61M 27/006* (2013.01)

(58) Field of Classification Search
CPC ...... A61K 31/00; A61K 31/165; A61K 31/18; A61K 31/202; A61K 31/225; A61K 31/28; A61K 31/405; A61K 31/4439; A61K 31/495; A61K 31/496; A61K 31/4995; A61K 31/5377; A61K 31/55; A61M 27/006
See application file for complete search history.

(56) References Cited

U.S. PATENT DOCUMENTS

2003/0013650 A1    1/2003 Liedtke et al.

OTHER PUBLICATIONS

International Search Report and Written Opinion issued by the ISA/US, Commissioner for Patents, dated Mar. 4, 2014, for International Application No. PCT/US2013/072758; 6 pages.
International Preliminary Report on Patentability issued by the International Bureau of WIPO, dated Jun. 9, 2015, for International Application No. PCT/US2013/072758; 5 pages.
Supplemental European Search Report issued by the European Patent Office (Munich), dated Jul. 21, 2016, for related Application No. EP13859760; 5 pages.
Examination report issued by the Australian Government, IP Australia, dated Aug. 29, 2017, for related Application No. AU2013356294; 2 pages.
Benfenati, Valentina et al., "An aquaporin-4/transient receptor potential vanilloid 4 (AQP4/TRPV4) complex is essential for cell-volume control in astrocytes," PNAS, vol. 108, No. 6, Feb. 8, 2011, pp. 2563-2568.
O'Callaghan, Christopher Liam et al., "The effect of viscous loading on brain ependymal cilia," Department of Infection, Immunity and Inflammation, University of Leicester, retrieved from the Internet Sep. 27, 2017: https://www.researchgate.net/publications/5340103_ The_effect_of_viscous_loading_on_brain_ependymal_cilia 16 pages.
Everaerts, Wouter et al., "The vanilloid transient receptor potential channel TRPV4: From structure to disease," Progress in Biophysics and Molecular Biology, vol. 103, Sep. 2010; 16 pages.
Harteneck, C., et al., "Functional Localization of the Osmosensor TRPV4 in the Apical Membrane of Plexus Choroideus," Article 233, XP009190680, Mar. 17, 2003; 1 page.
Takayama, Yasunori, "Functional linkage between TRPV4 and calcium-activated chloride channels in choroid plexus epithelial cells," Department of Physiological Science, 2013; 53 pages.
Vriens, Joris et al., "Pharmacology of Vanilloid Transient Receptor Potential Cation Channels," Molecular Pharmacology, vol. 75, No. 6, Feb. 16, 2009; pp. 1262-1279.
Gattone II, Vincent H., et al., "Development of Multiorgan Pathology in the wpk Rat Model of Polycystic Kidney Disease," The Anatomical Record, Part A 277A, (2004), pp. 384-395.

(Continued)

*Primary Examiner* — Kara R McMillian
(74) *Attorney, Agent, or Firm* — Faegre Baker Daniels LLP

(57) ABSTRACT

The present invention provides uses of TRPV4 antagonists in the treatment or prevention of hydrocephalus symptoms, also known as hydrocephaly, including hydrocephalus as a result of any structural defect, any metabolic defect, any injury (direct force to the head, indirect force to the head, shock waves, pressure changes, etc.), any insult (microbial, chemical, toxins, allergic reactions or other inflammatory process, or other pathology, eg. cancer, benign tumor, etc.). Related materials and methods are also provided herein.

15 Claims, 13 Drawing Sheets

(56) References Cited

OTHER PUBLICATIONS

Smith, Ursula M., et al., "The transmembrane protein meckelin (MKS3) is mutated in Meckel-Gruber syndrome and the wpk rat," Nature Genetics, vol. 38, No. 2, Feb. 2006, pp. 191-196.

Definition of Hydrocephalus, MayoClinic.com, available on the Internet, archived on Dec. 1, 2013, https://web.archive.org/web/20131201110740//http://www.mayoclinic.com/health/hydrocephalus/DS00393, 2 pages.

Causes of Hydrocephalus, MayoClinic.com, available on the Internet, archived on Jul. 30, 2013, https://web.archive.org/web/20130730131628//http://www.mayoclinic.com:80/health/hydrocephalus/DS00393/DSECTION=causes; 2 pages.

From WO2009/146177 (3 examples)

From WO2009/146182 (>25 examples)

From WO2010/011912 (>20 examples)

From WO2010/011914 (>200 examples)

2-Methyl-1-(3-morpholinopropyl)-5-phenyl-N-(3-(trifluoromethyl)phenyl)-1H-pyrrole-3-carboxamide.

RN-1734

Chemical Name: 2,4-Dichloro-N-isopropyl-N-(2-isopropylaminoethyl)benzenesulfonamide Phorbol esters as agonists of TRPV4.

4αPDD;  4αPDH;  deoxygenated version of 4αPDC

GSK101670A as a TRPV4 agonist

RN-1747 as a TRPV4 agonist

Lipid metabolites of the arachidonic acid serving as TRPV4 agonists 5,6-EET 8,9-EET

USE OF TRPV4 ANTAGONISTS TO AMELIORATE HYDROCEPHALUS AND RELATED MATERIALS AND METHODS

CROSS-REFERENCE TO RELATED APPLICATIONS

This application claims priority to International Application PCT/US2013/072,758 filed Dec. 3, 2013, which claims priority to U.S. Provisional Patent Application Ser. No. 61/732,708 filed Dec. 3, 2012 and to U.S. Provisional Patent Application Ser. No. 61/872,048 filed Aug. 30, 2013, the entire disclosures of which are expressly incorporated herein by reference.

BACKGROUND OF THE INVENTION

Hydrocephalus is the buildup of fluid (cerebrospinal fluid-CSF) within the ventricular system of the brain, sometimes referred to as "water on the brain." This is a serious condition that leads to neuronal death and long-term complications. CSF is produced by the choroid plexus (CP) which is an epithelial cell lined tuft of capillaries that project into the ventricles. The ventricle system is composed of four chambers, lateral ventricles (LV) within each of the cerebral hemispheres, the third ventricle connected to the lateral ventricles in the diencephalon (toward the base of the brain) and a fourth ventricle that is connected to the third ventricle by the cerebral aqueduct (of Sylvius). The CSF escapes from the fourth ventricle through three foramen (of Luschka and Magendie) into the subarachnoid space which surrounds the brain. CSF is reabsorbed into the venous blood by arachnoid granulations attached to the superior sagittal sinus which lies just under the cranial skullcap.

The CSF volume in the brain can be increased as a consequence of either: a) production of excess CSF, b) blocking the flow of CSF is (usually at the cerebral aqueduct) or c) insufficient reabsorption into the venous blood. The basic types of hydrocephalus are 1) communicating (that there is no blockage of flow so may be from over production or limited reabsorption) and noncommunicating (there is blockage to flow out of the brain ventricles).

In infants and children who develop hydrocephalus, the cranial sutures have not yet fused, so the cranium enlarges as the ventricles enlarge. In adults with hydrocephalus, the fused nature of the adult cranium results in increased pressure and tissue damage.

TRPV4 is a cilia-associated protein highly expressed in the ventricular system of the brain. TRPV4 (transient receptor potential vanilloid receptor 4) is one member of a large family of cation channels on the plasma membrane of epithelial and endothelial cells and is expressed in the lung, liver, kidney skin, sweat glands and central nervous system. TRPV4 is activated by changes in osmotic balance (hypotonicity) and mechanical stress (pressure) and, when activated, transports $Ca^{2+}$ into cells. TRPV4 is expressed by the ventricular ependyma of the choroid plexus that is responsible for cerebrospinal fluid (CSF) generation.

Cerebrospinal fluid is produced via an active process of secretion, which is different from the passive diffusion of water-containing fluids in other swelling-producing processes.

SUMMARY OF THE INVENTION

The present invention provides methods to ameliorate the symptoms of hydrocephalus in a patient, comprising administering at least one Transient Receptor Potential Vanilloid Receptor 4 (TRPV4) antagonist, or a pharmaceutically-acceptable salt thereof to a patient with symptoms of hydrocephalus and in need of symptom amelioration.

Also provided are methods to treat hydrocephalus in a patient, comprising administering at least one Transient Receptor Potential Vanilloid Receptor 4 (TRPV4) antagonist, or a pharmaceutically-acceptable salt thereof to a patient with hydrocephalus and in need of treatment.

Also provided are methods to prevent the symptoms of hydrocephalus in a patient, comprising administering at least one Transient Receptor Potential Vanilloid Receptor 4 (TRPV4) antagonist, or a pharmaceutically-acceptable salt thereof to a patient at risk of symptoms of hydrocephalus and in need prevention of symptoms.

Also provided are methods to reduce the risk of hydrocephalus in a patient with traumatic brain injury, comprising administering at least one Transient Receptor Potential Vanilloid Receptor 4 (TRPV4) antagonist, or a pharmaceutically-acceptable salt thereof to a patient with traumatic brain injury and in need of reducing the risk of hydrocephalus.

Also provided are methods to reduce the risk of hydrocephalus in a patient with at least one structural defect of the brain, comprising administering at least one Transient Receptor Potential Vanilloid Receptor 4 (TRPV4) antagonist, or a pharmaceutically-acceptable salt thereof to a patient with at least one structural defect of the brain and in need of reducing the risk of hydrocephalus.

Also provided are methods to reduce the risk of hydrocephalus in a patient with at least one metabolic defect of the brain, comprising administering at least one Transient Receptor Potential Vanilloid Receptor 4 (TRPV4) antagonist, or a pharmaceutically-acceptable salt thereof to a patient with at least one metabolic defect of the brain and in need of reducing the risk of hydrocephalus.

Also provided are methods to reduce the risk of hydrocephalus in a patient with brain inflammation, comprising administering at least one Transient Receptor Potential Vanilloid Receptor 4 (TRPV4) antagonist, or a pharmaceutically-acceptable salt thereof to a patient with brain inflammation and in need of reducing the risk of hydrocephalus.

Also provided are methods to reduce the risk of hydrocephalus in a patient with brain infection, comprising administering at least one Transient Receptor Potential Vanilloid Receptor 4 (TRPV4) antagonist, or a pharmaceutically-acceptable salt thereof to a patient with brain infection and in need of reducing the risk of hydrocephalus.

Also provided are methods to reduce the risk of hydrocephalus in a patient with brain damage, comprising administering at least one Transient Receptor Potential Vanilloid Receptor 4 (TRPV4) antagonist, or a pharmaceutically-acceptable salt thereof to a patient with brain damage and in need of reducing the risk of hydrocephalus.

Also provided are methods to reduce at least one symptom of hydrocephalus or risk thereof in a patient in need of such reduction, comprising administering at least one Transient Receptor Potential Vanilloid Receptor 4 (TRPV4) antagonist, or a pharmaceutically-acceptable salt thereof to a patient with at least one symptom of hydrocephalus or at risk thereof.

Also provided are methods herein, wherein the at least one symptom or risk thereof is due to a brain structure anomaly selected from the group consisting of: ventricular defect; aqueductal stenosis; genetic defect; developmental defect; spina bifida; encepholocele; premature birth; cranial lesion; holoprosencephaly; dilatation of the lateral ventricles of the brain; internal hydrocephalus; functional impairment of the arachnoidal granulations (also called arachnoid granulations or Pacchioni's granulations); enlarged cerebral ventricles; and myelomeningocele.

Also provided are methods herein, wherein at least one symptom or risk thereof is due to a syndrome selected from the group consisting of: Dandy-Walker Syndrome; Walker-Wardburg syndrome, Meckel syndrome, Smith-Lemli-Opitz syndrome, chondrodystrophies, trisomy 13, trisomy 18, triploidy, congenital heart disease and cleft lip and/or palate; mutation to the L1 cell adhesion molecule; MASA; CRASH; communicating hydrocephaly; non-communicating hydrocephaly; increased intracranial pressure; normal pressure hydrocephaly; impaired cerebrospinal fluid (CSF) flow; impaired CSF reabsorption; excessive CSF production; congenital absence of arachnoid villi; and type II Arnold-Chiari malformation.

Also provided are methods herein, wherein at least one symptom or risk thereof is due to an injury selected from the group consisting of: surgical trauma; blunt force trauma; stroke; intraventricular hemorrhage; subarachnoid hemorrhage; traumatic brain injury; scarring and/or fibrosis of the subarachnoid space; and intraventricular matrix hemorrhages in a premature infant.

Also provided are methods herein, wherein the at least one symptom or risk thereof is due to pathology selected from the group consisting of: meningitis; encephalitis; benign tumor; cancerous tumor; cancer; neoplasm; papilloma of choroid plexus; brain atrophy; dementia; schizophrenia; brain parenchyma loss; colloid cyst; atresia; normal pressure hydrocephalus (NPH); and ependymitis.

Also provided are methods herein, wherein the at least one symptom or risk thereof is due to a toxicity selected from the group consisting of: drug overdose; drug-drug interaction; poisoning; radiation; and idiopathic toxicity.

Also provided are methods herein, wherein the at least one symptom or risk thereof is due to an inflammatory process selected from the group consisting of: sepsis; allergy; and idiopathic inflammation.

Also provided are methods herein, wherein the at least one symptom or risk thereof is indicated by a symptom selected from the group consisting of: head circumference is enlarged; skull plates fail to fuse after third year in an infant; bulging, firm anterior and posterior fontanelles in an infant; upper eyelids become retracted and the eyes are turned downwards; seizures; headache followed by vomiting; nausea; papilledema (swelling of the optic disk which is part of the optic nerve); blurred or double vision; sunsetting of the eyes; problems with balance; poor coordination; gait disturbance; urinary incontinence; slowing or loss of developmental progress; lethargy, drowsiness, irritability, or other changes in personality or cognition including memory loss; impaired bladder control leading to urinary frequency and/or incontinence; and progressive mental impairment and dementia; progressive enlargement of the head; convulsion; tunnel vision; mental disability; Hakim's triad of gait instability; urinary incontinence and dementia; abducens nerve palsy; and vertical gaze palsy (Parinaud syndrome).

Also provided are methods herein, wherein the at least one symptom or risk thereof is indicated by parental behavior or attribute selected from the group consisting of: maternal obesity; low socioeconomic status of mother; lack of folate/folic acid in the maternal diet; maternal prenatal infection (toxoplasmosis, syphilis, cytomegalovirus, rubella, human lymphocytic choriomeningitis virus); parental toxin exposure (pesticide, poison, radiation, inflammagen); and maternal exposure to anesthesia.

Also provided are methods herein, wherein the at least one symptom or risk thereof is diagnosed via a method selected from the group consisting of: ultrasound; computed tomography (CT) scan; magnetic resonance imaging (MRI); radioisotope citernography; continuous intraventricular pressure recordings (over 24 hours or longer); and dynamic compliance studies.

Also provided are methods herein, wherein the patient is selected from the group consisting of: mouse; rat; guinea pig; cat; dog; monkey; horse; human.

Also provided are methods herein, wherein the TRPV4 antagonist is selected from the group consisting of: Ruthenium Red; RN-1734; RN-9893; capsazepine; citral; GSK205; HC-067047; any TRPV4 antagonist described in US 2011/0130400; GSK2193874; and any TRPV4 antagonist described US20110130400, WO_2009-111680, WO_2009-146177, WO_2009-146182, WO_2010-011912, WO_2010-011914, and/or WO_2011-119701.

Also provided are methods herein, which further comprises surgical placement of a CSF shunt.

Also provided are methods to identify compounds, formulations, combination therapies, and/or adjuvants useful for ameliorating hydrocephalus, comprising: administering a TRPV4 antagonist to a hydrocephalus test model, administering at least one test composition to the test model, inducing hydrocephalus in the test model, and identifying those compounds, formulations, combination therapies, and/or adjuvants useful for ameliorating hydrocephalus.

Also provided are compositions comprising at least one TRPV4 antagonist formulated for optimal blood-brain barrier passage.

Also provided are compositions herein, wherein the TRPV4 antagonist is selected from the group consisting of: Ruthenium Red; RN-1734; RN-9893; capsazepine; citral; GSK205; HC-067047; any TRPV4 TRPV4 antagonist described in US 2011/0130400; GSK2193874; and any TRPV4 antagonist described US20110130400, WO_2009-111680, WO_2009-146177, WO_2009-146182, WO_2010-011912, WO_2010-011914, and/or WO_2011-119701.

Also provided are compositions herein which are selected from the group consisting of: PEGylated TRPV4 antagonist; TRPV4 antagonist nanoparticle; TRPV4 antagonist liposome; TRPV4 antagonist immunoliposome.

Also provided are methods to induce the symptoms of hydrocephalus in an animal test model, comprising administering at least one Transient Receptor Potential Vanilloid Receptor 4 (TRPV4) agonist, or a pharmaceutically-acceptable salt thereof to an animal test model.

Also provided are methods herein, wherein the TRPV4 agonist is selected from the group consisting of: phorbol esters; GSK101670A; RN-1747; and lipid metabolites of the arachidonic acid.

Also provided are methods to identify compounds, formulations, combination therapies, and/or adjuvants useful for ameliorating hydrocephalus, comprising: administering a TRPV4 agonist to a hydrocephalus test model, administering at least one test composition to the test model, inducing hydrocephalus in the test model, and identifying those compounds, formulations, combination therapies, and/or adjuvants useful for ameliorating hydrocephalus.

Various aspects of this invention will become apparent to those skilled in the art from the following detailed description of the preferred embodiment, when read in light of the accompanying figures.

DETAILED DESCRIPTION OF THE INVENTION

Figure 1:
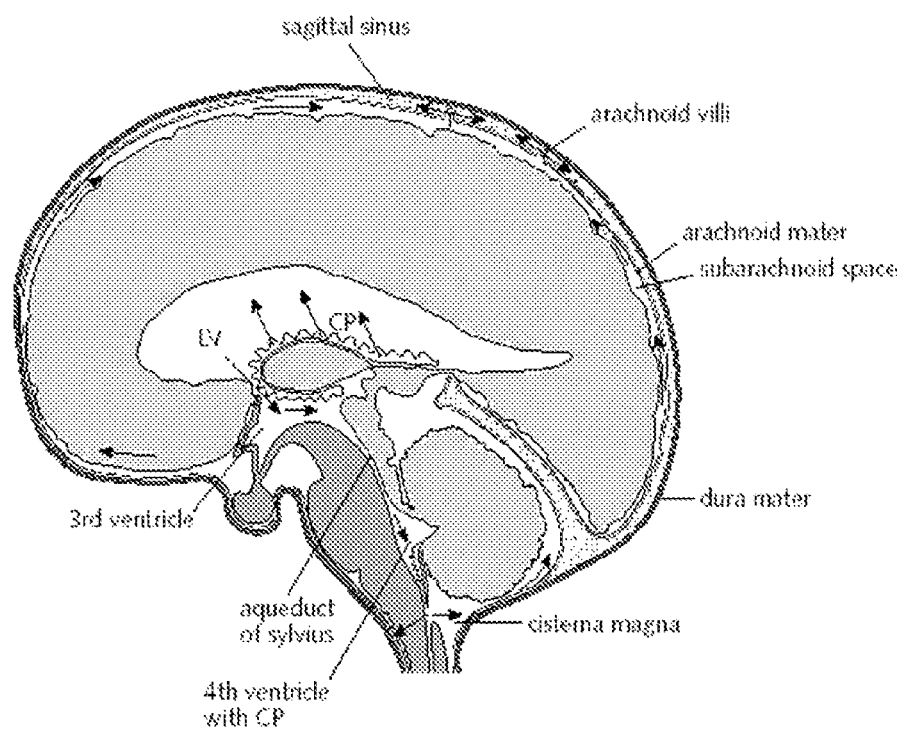
FIG. 1. Schematic of the ventricular system of the human brain.

While studying the effect of TRPV4 agonists and antagonists on the renal cystic disease, the present inventors made the serendipitous observation that while the TRPV4 modulators did not alter the course of the cystic renal disease, the antagonists did alleviate the degree of hydrocephaly in the affected animals. This unexpected observation led to further studies which showed that two structurally distinct TRPV4 antagonists can ameliorate the symptoms of hydrocephalus.

Hydrocephalus

By "hydrocephalus" we include any hydrocephalus occurring in the fetal or neonatal period including, but not limited to, Early Onset hydrocephalus (EOHC), Fetal Onset hydrocephalus, Congenital hydrocephalus, Obstructive hydrocephalus, Communicating hydrocephalus.

Also included is any hydrocephalus resulting from structural defects in the brain, including but not limited to, ventricular defect; aqueductal stenosis; genetic defect; developmental defect; spina bifida; encepholocele; premature birth; cranial lesion; holoprosencephaly; dilatation of the lateral ventricles of the brain; internal hydrocephalus; functional impairment of the arachnoidal granulations (also called arachnoid granulations or Pacchioni's granulations); enlarged cerebral ventricles; and myelomeningocele.

Also included is any hydrocephalus occurring as a result of metabolic defects, including, but not limited to Dandy-Walker Syndrome; Walker-Wardburg syndrome, Meckel syndrome, Smith-Lemli-Opitz syndrome, chondrodystrophies, trisomy 13, trisomy 18, triploidy, congenital heart disease and cleft lip and/or palate; mutation to the L1 cell adhesion molecule; MASA; CRASH; communicating hydrocephaly; non-communicating hydrocephaly; increased intracranial pressure; normal pressure hydrocephaly; impaired cerebrospinal fluid (CSF) flow; impaired CSF reabsorption; excessive CSF production; congenital absence of arachnoid villi; and type II Arnold-Chiari malformation.

Also included is any hydrocephalous occurring as a result of brain injury, including but not limited to, surgical trauma; blunt force trauma; stroke; intraventricular hemorrhage; subarachnoid hemorrhage; traumatic brain injury; scarring and/or fibrosis of the subarachnoid space; and intraventricular matrix hemorrhages in a premature infant.

Also included is any hydrocephalus occurring as a result of pathological conditions, including, but not limited to, meningitis; encephalitis; benign tumor; cancerous tumor; cancer; neoplasm; papilloma of choroid plexus; brain atrophy; dementia; schizophrenia; brain parenchyma loss; colloid cyst; atresia; normal pressure hydrocephalus (NPH); and ependymitis.

Also included is any hydrocephalous occurring as a result of toxicities including, but not limited to, drug overdose; drug-drug interaction; poisoning; radiation; and idiopathic toxicity.

Also included is any hydrocephalus occurring as a result brain inflammations, including, but not limited to, sepsis; allergy; and idiopathic inflammation.

Developmental Hydrocephalus

There are many causes of developmental hydrocephalus, including neural tube defects and other congenital abnormalities. There are currently no treatments for developmentally-related hydrocephalus other than placement of shunts to drain fluid from the brain to other parts of the body where it can be reabsorbed. In the pediatric population, long-term shunt placement necessitates removal and replacement as the child grows. Unfortunately this is not an optimal treatment and is associated with infections and shunt obstructions leading to shunt failures as high as 50% within two years.

Injury/Insult Hydrocephalus

Post-traumatic hydrocephalus is a serious complication of traumatic brain injury and has been estimated to occur in as many as 50% of traumatic brain injury cases. Whether this type of injury happens on a battleground, football field or after a car accident, the resulting post traumatic hydrocephalus contributes to neuronal death and long lasting complications. The only treatment option for this form of hydrocephalus is also surgical internal or external shunt placement.

Insult hydrocephalus may occur via intraventricular hemorrhage, inflammatory infections, or pathological states, including tumors. The result is the same as traumatic brain injuries: neuronal death and complications. Again, although the underlying insult may be treatable with pharmaceutical therapies, the hydrocephalus is managed by the placement of shunts.

In this regard, hydrocephalus due to injury or chemical/biological insult is almost often unanticipated and emergent, with neuronal damage correlating with delay in treatment. Since shunts are the only current therapy for these types of hydrocephalus, the period from identification of trauma and/or insult and presentation to a surgery center becomes critical. The present invention provides in-field options, which reduces neuronal cell death. The present treatments are therefore not only less invasive and risky compared to surgery, they are also less burdensome to the health care system.

The present invention provides significant amelioration of the hydrocephalic cranial enlargement and results in less severe disease. The present invention provides a reduction of the ventricular enlargement associated with inherited, developmental, injury, or insult hydrocephalus.

Any known or future TRPV4 antagonists, or combination of TRPV4 antagonists, are useful in the present invention, including these known TRPV4 antagonists: Ruthenium Red, RN-1734, RN-9893, capsazepine, citral, GSK205, HC-067047, GSK2193874 and any TRPV4 antagonist described in US20110130400, WO_2009-111680, WO_2009-146177, WO_2009-146182, WO_2010-011912, WO_2010-011914, and/or WO_2011-119701 (the disclosures of each and all are hereby incorporated by reference).

Methods of Use

The present invention discloses the use of TRPV4 antagonists in the treatment or prevention of hydrocephalus, also known as hydrocephaly, including hydrocephalus as a result of any structural defect, any metabolic defect, any injury (direct force to the head, indirect force to the head, shock waves, pressure changes, altitude changes, etc.), any insult (microbial, chemical, toxins, poisons, radioactivity, allergic reactions or other inflammatory process, or other pathology, eg. cancer, benign tumor, etc.). Accordingly, in another aspect the invention is directed to methods of treating such conditions.

The methods of treatment of the invention comprise administering a safe and effective amount of a TRPV4 antagonist or a pharmaceutically-acceptable salt thereof to a patient in need thereof.

As used herein, "treat" in reference to a condition means: (1) to ameliorate or prevent the condition or one or more of the biological manifestations of the condition, (2) to interfere with (a) one or more points in the biological cascade that leads to or is responsible for the condition or (b) one or more of the biological manifestations of the condition, (3) to alleviate one or more of the symptoms or effects associated with the condition, or (4) to slow the progression of the condition or one or more of the biological manifestations of the condition.

As indicated above, "treatment" of a condition includes prevention of the condition. The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof.

As used herein, "safe and effective amount" in reference to a compound of the invention or other pharmaceutically-active agent means an amount of the compound sufficient to treat the patient's condition but low enough to avoid serious side effects (at a reasonable benefit/risk ratio) within the scope of sound medical judgment. A safe and effective amount of a compound will vary with the particular compound chosen (e.g. consider the potency, efficacy, and half-life of the compound); the route of administration chosen; the condition being treated; the severity of the condition being treated; the age, size, weight, and physical condition of the patient being treated; the medical history of the patient to be treated; the duration of the treatment; the nature of concurrent therapy; the desired therapeutic effect; and like factors, but can nevertheless be routinely determined by the skilled artisan.

As used herein, "patient" or "subject" means an individual having symptoms of, or at risk for, hydrocephalus or other malignancy. A patient may be human or non-human and may include, for example, animal strains or species used as "model systems" for research purposes, such a mouse model as described herein. Likewise, patient may include either adults or juveniles (e.g., children). Moreover, patient may mean any living organism, preferably a mammal (e.g., human or non-human) that may benefit from the administration of TRPV4 antagonists contemplated herein.

Compositions

TRPV4 antagonists can be formulated into compositions which may be administered by the oral and rectal routes, topically, by intrathecal or intracranial injections, parenterally, e.g., by injection and by continuous or discontinuous intra-arterial infusion, in the form of, for example, tablets, lozenges, sublingual tablets, sachets, cachets, elixirs, gels, suspensions, aerosols, ointments, for example, containing from 1 to 10% by weight of the active compound in a suitable base, soft and hard gelatin capsules, suppositories, injectable solutions and suspensions in physiologically acceptable media, and sterile packaged powders adsorbed onto a support material for making injectable solutions. Advantageously for this purpose, compositions may be provided in dosage unit form, preferably each dosage unit containing from about 1 mg to about 1000 mg (from about 5 mg to about 50 mg in the case of parenteral or inhalation administration, and from about 25 to about 500 mg in the case of oral or rectal administration) the compounds. Dosages from about 0.5 to about 300 mg/kg per day, of active ingredient may be administered although it will, of course, readily be understood that the amount of the compound actually to be administered will be determined by a physician, in light of all the relevant circumstances including the condition to be treated, the choice of compound to be administered, and the choice of route of administration. In one embodiment the dose of MS-153 is about 20 mg/kg/day to about 50 mg/kg/day. The dosage ranges discussed herein are not intended to limit the scope of the present invention in any way.

The TRPV4 antagonists may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan. In addition, suitable dosing regimens, including the duration such regimens are administered, for a compound of the invention depend on the condition being treated, the severity of the condition being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

Additionally, the TRPV4 antagonists may be administered as prodrugs. As used herein, a "prodrug" of a TRPV4 antagonists is a functional derivative of the compound which, upon administration to a patient, eventually liberates the compound of the invention in vivo. Administration of a compound of the invention as a prodrug may enable the skilled artisan to do one or more of the following: (a) modify the onset of the compound in vivo; (b) modify the duration of action of the compound in vivo; (C) modify the transportation or distribution of the compound in vivo; (d) modify the solubility of the compound in vivo; and (e) overcome or overcome a side effect or other difficulty encountered with the compound. Typical functional derivatives used to prepare prodrugs include modifications of TRPV4 antagonists that are chemically or enzymatically cleaved in vivo. Such modifications, which include the preparation of phosphates, amides, esters, thioesters, carbonates, and carbamates, are well known to those skilled in the art.

The pharmaceutical compositions of the invention may be prepared and packaged in bulk form wherein a safe and effective amount of a compound of the invention can be extracted and then given to the patient such as with powders or syrups. Alternatively, the pharmaceutical compositions of the invention may be prepared and packaged in unit dosage form wherein each physically discrete unit contains a safe and effective amount of at least one TRPV4 antagonist. When prepared in unit dosage form, the pharmaceutical compositions of the invention typically contain from 1 mg to 1000 mg.

The pharmaceutical compositions of the invention typically contain one TRPV4 antagonist. However, in certain embodiments, the pharmaceutical compositions of the invention contain more than one TRPV4 antagonist. For example, in certain embodiments the pharmaceutical compositions of the invention contain two TRPV4 antagonists. In addition, the pharmaceutical compositions of the invention may optionally further comprise one or more additional pharmaceutically active compounds.

As used herein, "pharmaceutically-acceptable excipient" means a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of the invention when administered to a patient and interactions which would result in pharmaceutical compositions that are not pharmaceutically acceptable are avoided. In addition, each excipient must of course be of sufficiently high purity to render it pharmaceutically-acceptable.

The TRPV4 antagonist(s) and the pharmaceutically-acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as dry powders, aerosols, suspensions, and solutions; (6) topical administration such as creams, ointments, lotions, solutions, pastes, sprays, foams, and gels; and (7) intracranial or intrathecal injection.

Suitable pharmaceutically-acceptable excipients will vary depending upon the particular dosage form chosen. In addition, suitable pharmaceutically-acceptable excipients may be chosen for a particular function that they may serve in the composition. For example, certain pharmaceutically-acceptable excipients may be chosen for their ability to facilitate the production of uniform dosage forms. Certain pharmaceutically-acceptable excipients may be chosen for their ability to facilitate the production of stable dosage forms. Certain pharmaceutically-acceptable excipients may be chosen for their ability to facilitate the carrying or transporting of the compositions of the invention once administered to the patient from one organ, or portion of the body, to another organ, or portion of the body. Certain pharmaceutically-acceptable excipients may be chosen for their ability to enhance patient compliance.

Suitable pharmaceutically-acceptable excipients include the following types of excipients: Diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically-acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

The pharmaceutical compositions of the invention are prepared using techniques and methods known to those skilled in the art. Some of the methods commonly used in the art are described in Remington's Pharmaceutical Sciences (Mack Publishing Company).

In one aspect, the invention is directed to a solid oral dosage form such as a tablet or capsule comprising a safe and effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

The compounds may be administered alone or in conjunction with one or more other therapeutic agents, said agents optionally being one or more carbonic anhydrase inhibitors, such as acetazolamide, methazolamide, dorzolamide, topiramate and any elligatannins, such as punicalin, punicalagin, granatin B, gallagyldilactone, casuarinin, pedunculagin and tellimagrandin I.

The compounds may be administered alone or in conjunction with one or more other therapeutic agents, said agents optionally being one or more edema treatments.

The compounds may be administered with compositions that assist or increase the transport of the drug across the blood brain barrier, to provide increased access of the drug to the brain. Some brain targeting strategies involve: a) exploiting endogenous transporters for carrier mediated uptake (e.g. monoclonal antibody—drug conjugates or monoclonal antibody—particle conjugates) to exploit the human insulin or transferrin receptor; b) the inhibition of ABC transporters (e.g. P-glycoprotein and breast cancer resistance protein); c) the use of surfactant coated poly (butylcyanoacrylate) nanoparticles; and d) the use of cationic carriers such as cationic albumin and cationised forms of drug molecules.

Symptoms of Hydrocephalus

In another aspect, a method to reduce at least one symptom of hydrocephalus in a patient is provided, the method comprising administering to the patient in need thereof, a safe and effective amount at least one Transient Receptor Potential Vanilloid Receptor 4 (TRPV4) antagonists, or a pharmaceutically-acceptable salt thereof.

Symptoms of hydrocephalus vary with age, disease progression, and individual differences in tolerance to the condition. For example, an infant's ability to compensate for increased CSF pressure and enlargement of the ventricles differs from an adult's. The infant skull can expand to accommodate the buildup of CSF because the sutures (the fibrous joints that connect the bones of the skull) have not yet closed.

In infancy, the most obvious indication of hydrocephalus is often a rapid increase in head circumference or an unusually large head size. Other symptoms may include vomiting, sleepiness, irritability, downward deviation of the eyes (also called "sunsetting"), and seizures.

Older children and adults may experience different symptoms because their skulls cannot expand to accommodate the buildup of CSF. Symptoms may include headache followed by vomiting, nausea, papilledema (swelling of the optic disk which is part of the optic nerve), blurred or double vision, sunsetting of the eyes, problems with balance, poor coordination, gait disturbance, urinary incontinence, slowing or loss of developmental progress, lethargy, drowsiness, irritability, or other changes in personality or cognition including memory loss.

Symptoms of normal pressure hydrocephalus include, problems with walking, impaired bladder control leading to urinary frequency and/or incontinence, and progressive mental impairment and dementia. A patient with this type of hydrocephalus may have a general slowing of movements or may complain that his or her feet feel "stuck." Doctors may use a variety of tests, including brain scans (CT and/or MRI), a spinal tap or lumbar catheter, intracranial pressure monitoring, and neuropsychological tests, to help them accurately diagnose normal pressure hydrocephalus and rule out any other conditions.

The symptoms described in this section account for the most typical ways in which progressive hydrocephalus manifests itself, but it is important to remember that symptoms vary significantly from one person to the next.

The symptoms may be indicated by, including, but not limited to, head circumference is enlarged, skull plates fail to fuse after third year in an infant, bulging, firm anterior and posterior fontanelles in an infant, upper eyelids become retracted and the eyes are turned downwards, seizures, headache followed by vomiting, nausea, papilledema (swelling of the optic disk which is part of the optic nerve), blurred or double vision, sunsetting of the eyes, problems with balance, poor coordination, gait disturbance, urinary incontinence, slowing or loss of developmental progress, lethargy, drowsiness, irritability, or other changes in personality or cognition including memory loss, impaired bladder control leading to urinary frequency and/or incontinence, and progressive mental impairment and dementia, progressive enlargement of the head, convulsion, tunnel vision, mental disability, Hakim's triad of gait instability, urinary incontinence and dementia, abducens nerve palsy, and vertical gaze palsy (Parinaud syndrome).

The symptoms may also be diagnosed by, including, but not limited to, ultrasound, computed tomography (CT) scan, magnetic resonance imaging (MRI), radioisotope citernography, continuous intraventricular pressure recordings (over 24 hours or longer), and dynamic compliance studies.

In an additional aspect, a method of reducing the risk of hydrocephalus in a patient is provided, the method comprising administering at least one TRPV4 antagonist, or a pharmaceutically acceptable salt thereof to a patient in need thereof.

The risk of hydrceophalus in a patient is can be caused by traumatic brain injury, structural defects in the brain, metabolic defects of the brain, brain inflammation, brain infection, toxicity, pathological condition and brain damage, or combinations thereof, as described above.

In addition, the risk for hydrocephalus may be indicated by parental behavior or attribute including, but not limited to, maternal obesity, low socioeconomic status of mother, lack of folate/folic acid in the maternal diet, maternal prenatal infection (toxoplasmosis, syphilis, cytomegalovirus, rubella, human lymphocytic choriomeningitis virus), parental toxin exposure (pesticide, poison, radiation, inflammagen), and maternal exposure to anesthesia.

The principle and mode of operation of this invention have been explained and illustrated in its preferred embodiment. However, it must be understood that this invention may be practiced otherwise than as specifically explained and illustrated without departing from its spirit or scope.

EXAMPLES

Example 1. Materials and Methods

Wistar Wpk/Wpk rats are an orthologous model of human type 3 Meckel Syndrome. Meckel Syndrome is a cilliopathology with both renal cystic and brain pathology. The brain pathology is severe hydrocephalus with hypoplasia of the corpus callosum.

Example 2. TRPV4 Agonist and Antagonist Introduction to Wpk/Wpk Rats

The inventors treated Wpk/Wpk affected as well as noncystic littermates with either TRPV4 agonist (GSK1016797, 0.003 mg/kg body weight) or antagonist (HC067047, 0.03 mg/kg) from day 8 through 17 and evaluated the cranial enlargement and cerebral manifestations. Both drugs were dissolved in DMSO prior to dilution with normal saline prior to injection (i.p.).

Figure 2:
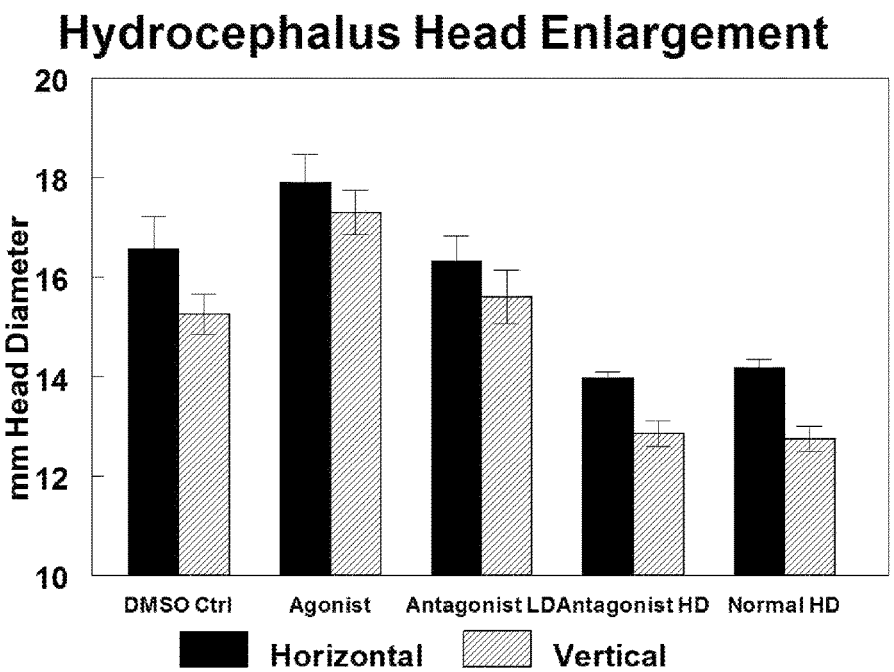
FIG. 2. Hydrocephalus head enlargement of rat model under various treatments. The antagonist treatment limited the brain and cranial enlargement so that the rats were equivalent to what was found in nonaffected littermates (Mean+SEM, *=<0.01 for difference from DMSO control, **=<0.001 for difference from TRPV4 agonist treatment, there was no difference in head dimensions between TRPV4 antagonist treatment in affected versus normal littermates).
Figure 3:
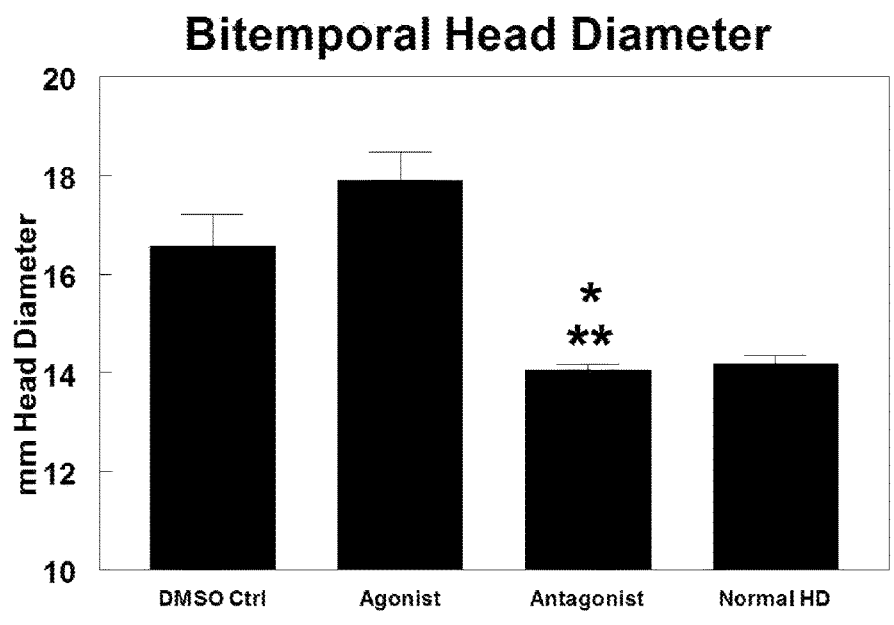
FIG. 3. Bitemporal head diameter of rat model under various treatments.
Figure 4:
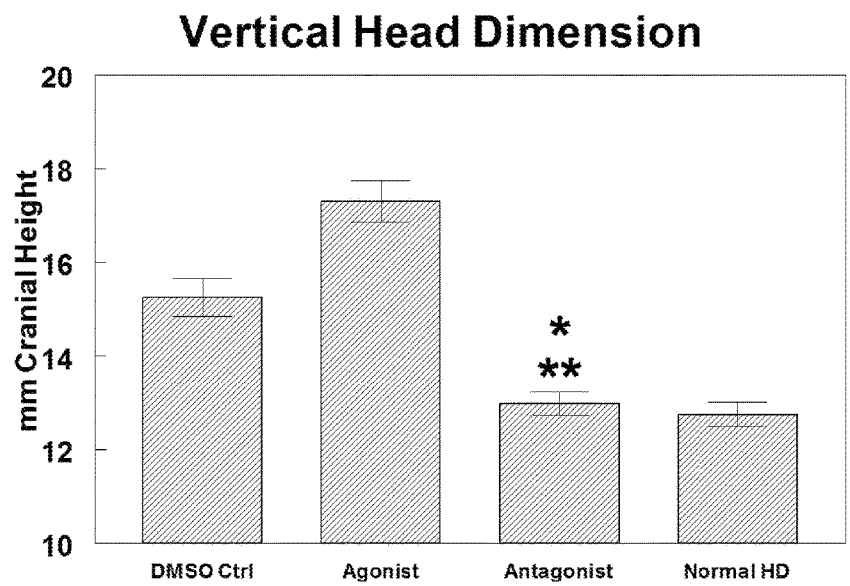
FIG. 4. Vertical head dimension of rat model under various treatments.
Figure 5:
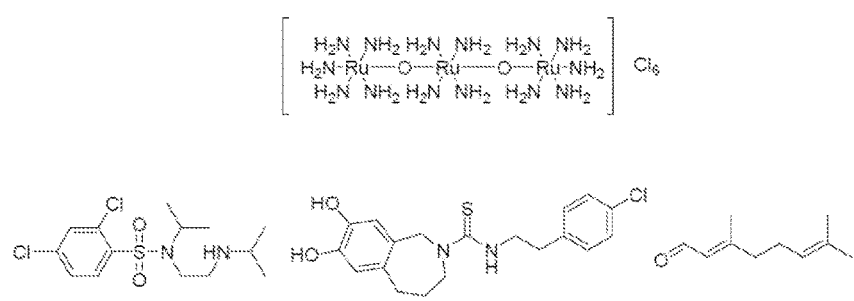
FIG. 5. Illustrative TRPV4 antagonists.
Figure 6:
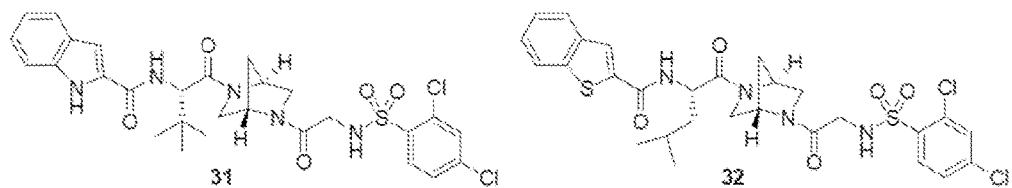
FIG. 6. Illustrative TRPV4 antagonists.
Figure 6:
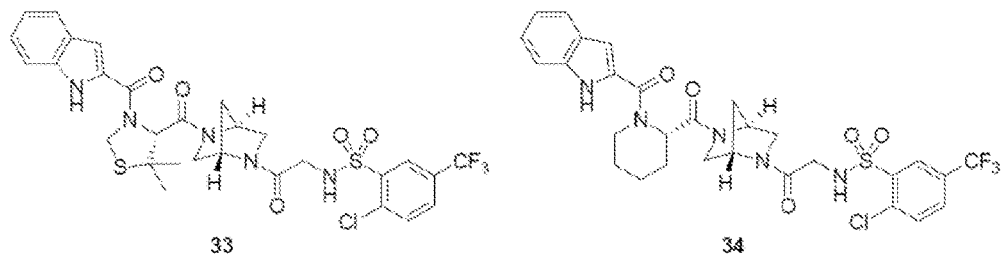
Figure 6:
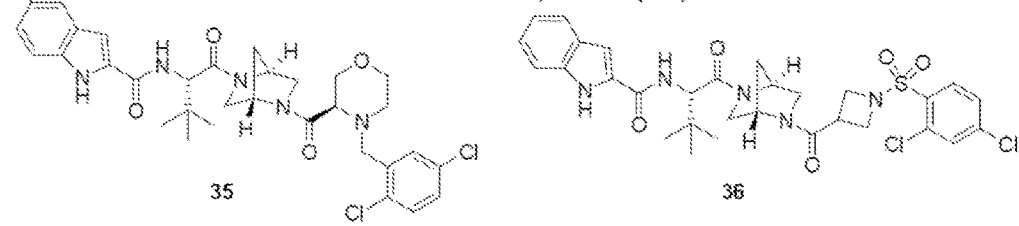
Figure 6:
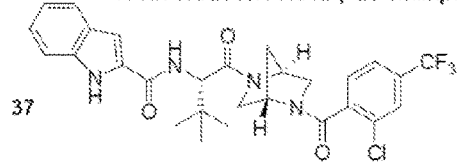
Figure 6:
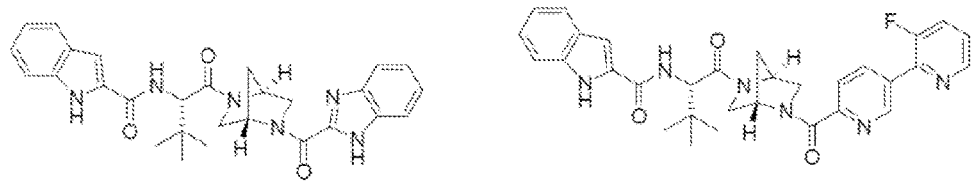
Figure 7:
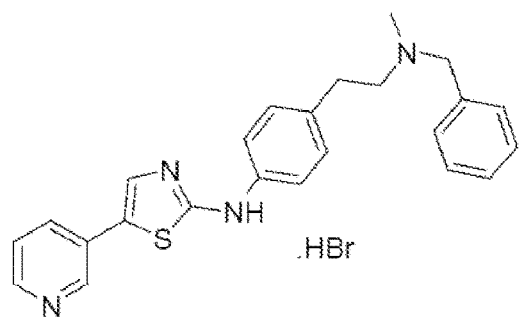
FIG. 7. Illustrative TRPV4 antagonist.
Figure 8:
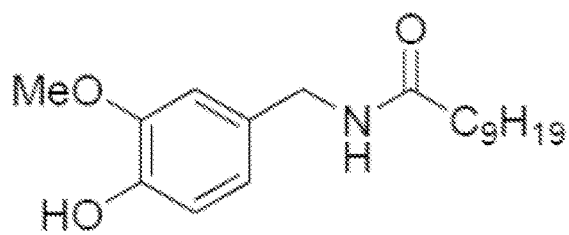
FIG. 8. Illustrative TRPV4 antagonist.
Figure 9:
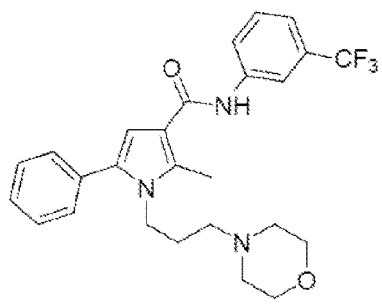
FIG. 9. Illustrative TRPV4 antagonist.
Figure 10:
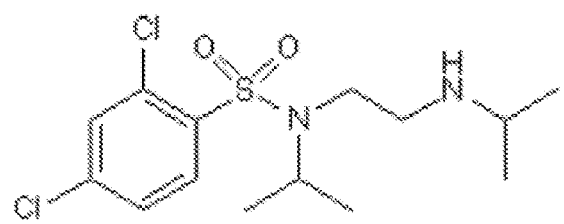
FIG. 10. Illustrative TRPV4 antagonist RN-1734.
Figure 11:
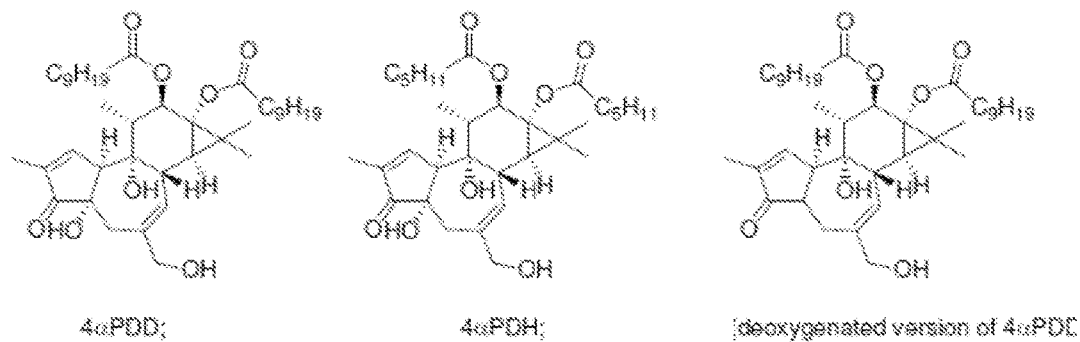
FIG. 11. Illustrative TRPV4 agonist.
Figure 12:
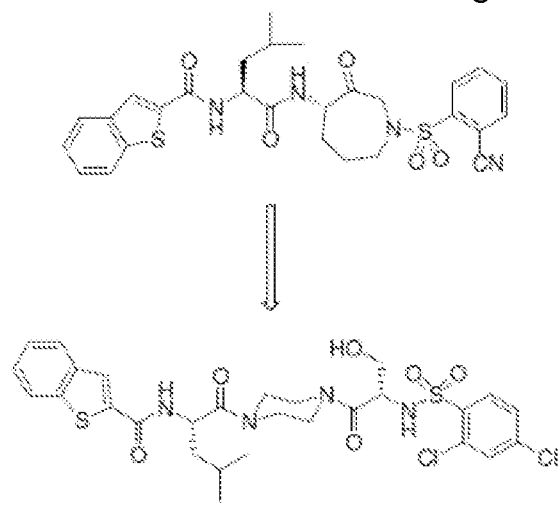
FIG. 12. Illustrative TRPV4 agonists.
Figure 13:
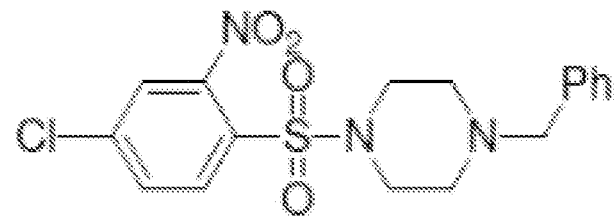
FIG. 13. Illustrative TRPV4 agonist.
Figure 14:
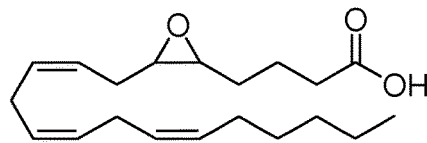
FIG. 14. Illustrative TRPV4 agonists.
Figure 14:
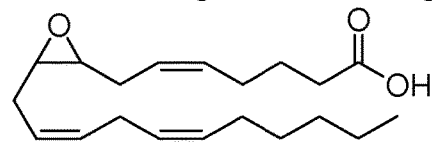
Figure 15:
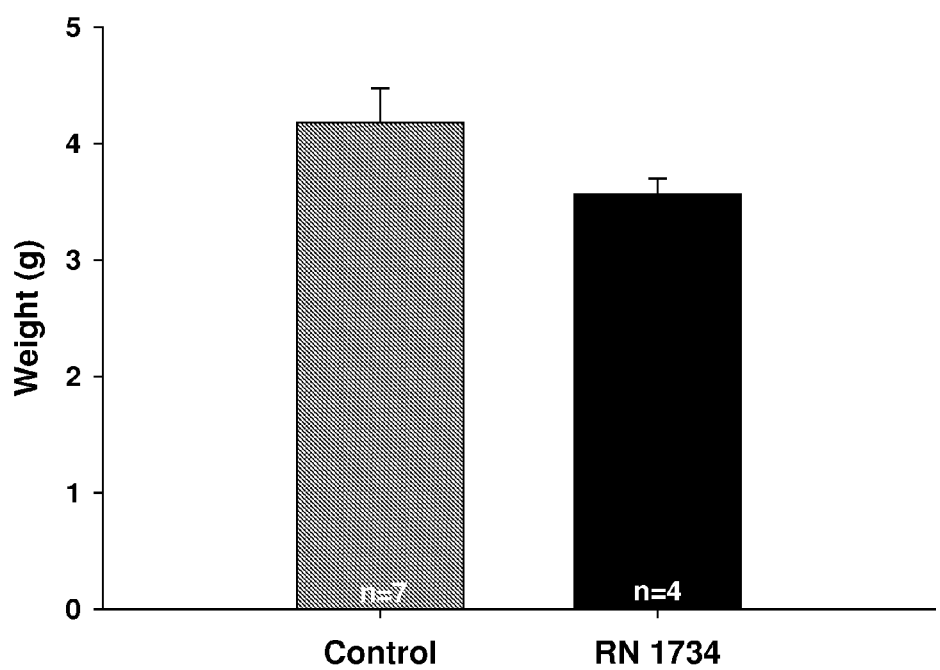
FIG. 15. Effect of RN-1734 on total kidney weight.
Figure 16:
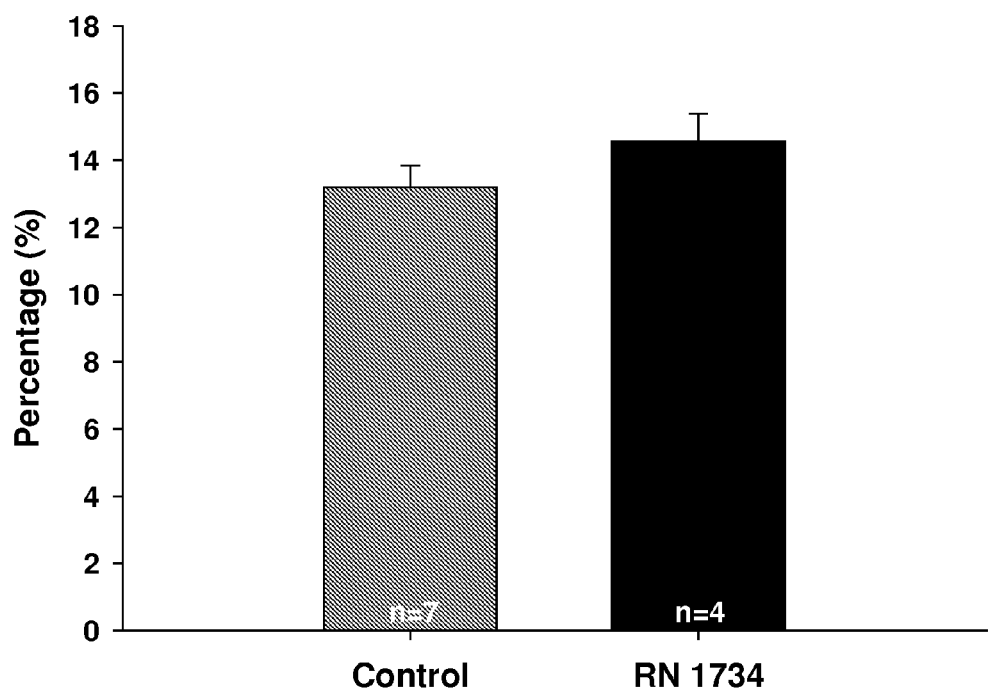
FIG. 16. Effect of RN-1734 on kidney weight as a percentage of body weight.
Figure 17:
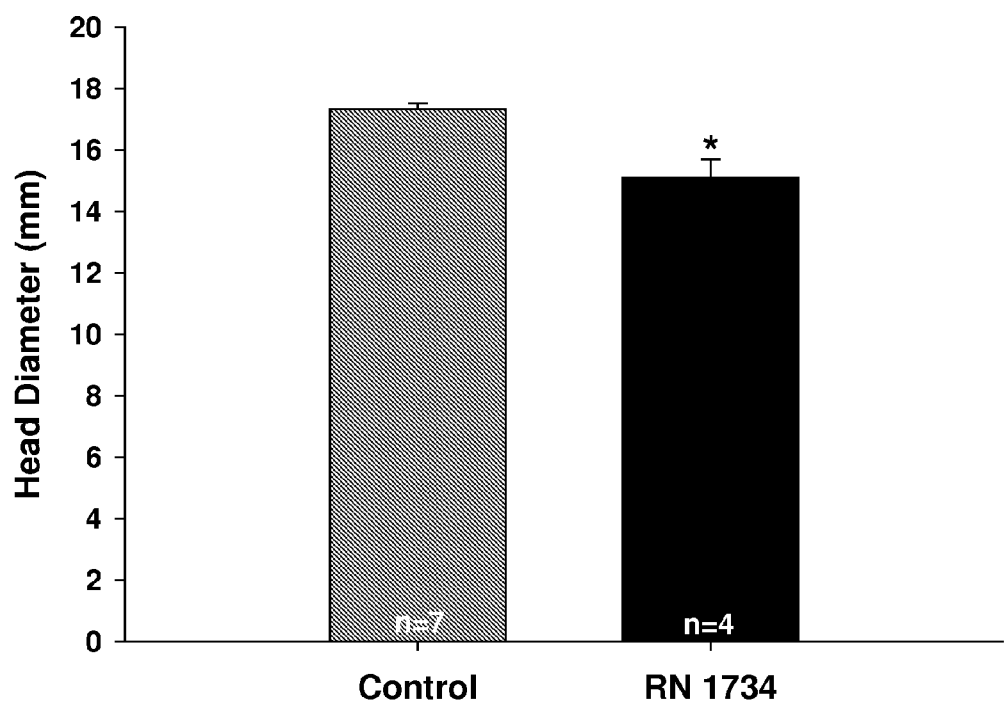
FIG. 17. Effect of RN-1734 on bitemporal head diameter.
Figure 18:
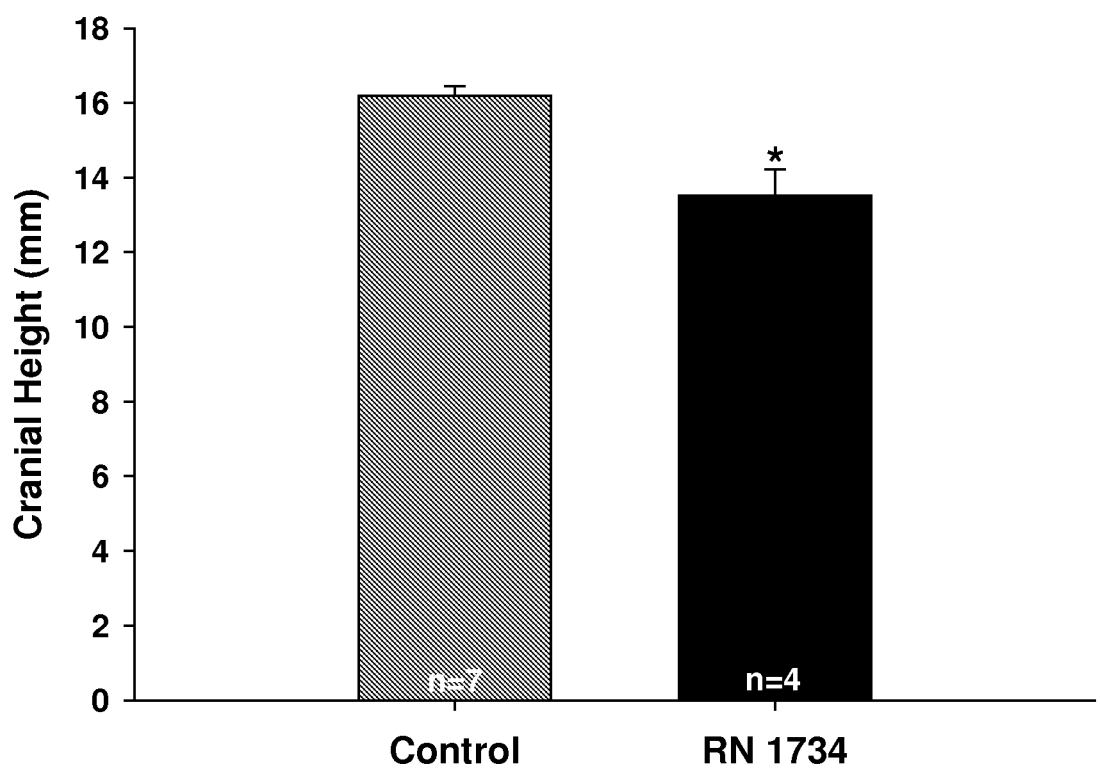
FIG. 18. Effect of RN-1734 on vertical head dimension.
Figure 19:
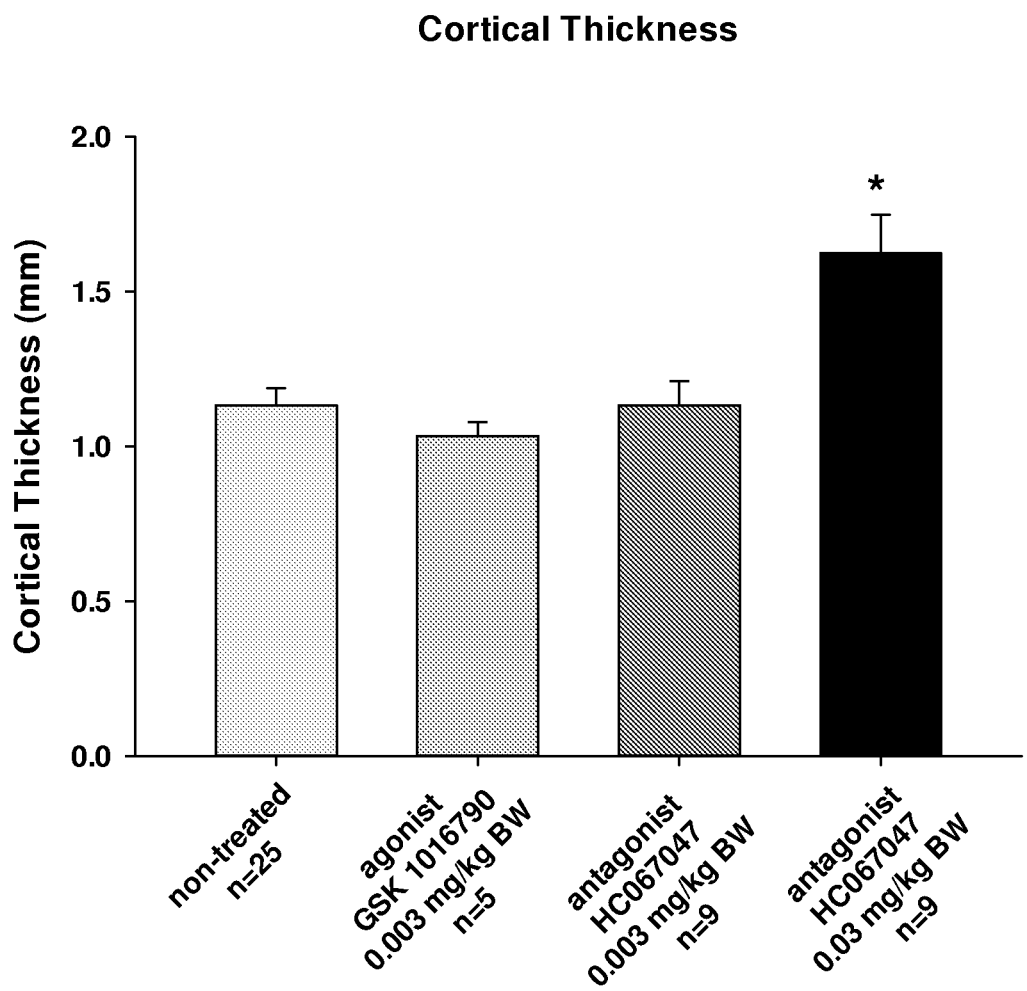
FIG. 19. Effect of TRPV antagonists on cortical thickness.

The cranial enlargement at day 17 of agonist treatment was sufficiently severe to require termination. However, treatment with the specific TRPV4 antagonist appears to almost totally ameliorate the hydrocephalic enlargement of the cranium/brain. The antagonist treated rats were also very active and alert like their nonaffected littermates. Treatments did not affect the renal pathology, only the cerebral pathology. FIGS. 2, 3, and 4 show the results.

The antagonist treatment limited the brain and cranial enlargement so that the rats were equivalent to their nonaffected littermates (Mean+SEM, *=<0.01 for difference from DMSO control, **=<0.001 for difference from TRPV4 agonist treatment, there was no difference in head dimensions between TRPV4 antagonist treatment in affected versus normal littermates).

HC067047 TRPV4 antagonist treatment resulted in significantly less hydrocephalic head measurements compared to littermates. FIGS. 2, 3, and 4 show the results.

Example 3. Effect of TRPV4 Antagonist RN-1734 in Wpk/Wpk Rats

Wpk/Wpk affected as well as noncystic littermates were treated with TRPV4 antagonist RN-1734 from day 8 through 17 and evaluated the kidney weight and cerebral manifestations (bitemporal head diameter and vertical head dimensions/cranial height). Both drugs were dissolved in DMSO prior to dilution with normal saline prior to injection (i.p.).

Treatment with the specific TRPV4 antagonist appears to almost totally ameliorate the hydrocephalic enlargement of the cranium/brain. The antagonist treated rats were also very active and alert like their nonaffected littermates. Treatments did not affect the renal pathology, only the cerebral pathology. FIGS. 15, 16, 17, and 18 show the results.

The antagonist treatment limited the brain and cranial enlargement so that the rats were equivalent to their nonaffected littermates (Mean+SEM, *=<0.01 for difference from DMSO control, there was no difference in head dimensions between TRPV4 antagonist treatment in affected versus normal littermates).

Example 4. Effect of TRPV4 Antagonists on Cortical Thickness

Cortical thickness measured from coronal sections of Wpk/Wpk hydrocephalic rats at day 17. Animals treated with 0.03 mg/kg body weight of the HC067047 TRPV4 antagonist (day 8-17) showed increased cortical thickness. * p<0.0001. This finding is in agreement with the decreased degree of hydrocephalus in the antagonist treated animals and, therefore, have a decreased loss in cerebral cortex.

What is claimed is:

1. A method to slow the progression of or ameliorate hydrocephalus in a patient in need thereof, the method comprising:
   a) administering a safe and effective amount of at least one Transient Receptor Potential Vanilloid Receptor 4 (TRPV4) antagonist, or a pharmaceutically-acceptable salt thereof, to the patient, wherein the at least one TRPV4 antagonist is RN-1734, HC-067047, or both RN-1734 and HC-067047; and
   b) slowing the progression of or ameliorating hydrocephalus in the patient.

2. The method of claim 1, wherein the patient is selected from the group consisting of: mouse; rat; guinea pig; cat; dog; monkey; horse; and human.

3. The method of claim 1, further comprising surgical placement of a cerebral spinal fluid (CSF) shunt in the patient.

4. The method of claim 1, wherein the hydrocephalus results from a cause selected from the group consisting of: traumatic brain injury; at least one structural defect in the brain; at least one metabolic defect of the brain; brain inflammation; brain infection; toxicity; a pathological condition; and brain damage.

5. The method of claim 1, wherein the hydrocephalus is caused by at least one structural defect in the brain selected from the group consisting of: ventricular defect; aqueductal stenosis; genetic defect; developmental defect; spina bifida; encepholocele; premature birth; cranial lesion; holoprosencephaly; dilatation of the lateral ventricles of the brain; internal hydrocephalus; functional impairment of the arachnoidal granulations; enlarged cerebral ventricles; and myelomeningocele.

6. The method of claim 1, wherein the hydrocephalus is caused by at least one metabolic defect selected from the group consisting of: Dandy-Walker Syndrome; Walker-Wardburg syndrome, Meckel syndrome, Smith-Lemli-Opitz syndrome; chondrodystrophies; trisomy 13; trisomy 18; triploidy; congenital heart disease and cleft lip and/or palate; mutation to the L1 cell adhesion molecule; MASA; CRASH; communicating hydrocephaly; non-communicating hydrocephaly; increased intracranial pressure; normal pressure hydrocephaly; impaired cerebrospinal fluid (CSF) flow; impaired CSF reabsorption; excessive CSF production; congenital absence of arachnoid villi; and type II Arnold-Chiari malformation.

7. The method of claim 1, wherein the hydrocephalus is caused by at least one brain injury selected from the group consisting of: surgical trauma; blunt force trauma; stroke; intraventricular hemorrhage; subarachnoid hemorrhage; traumatic brain injury; scarring and/or fibrosis of the subarachnoid space; and intraventricular matrix hemorrhages in a premature infant.

8. The method of claim 1, wherein the hydrocephalus is caused by at least one pathological condition selected from the group consisting of: meningitis; encephalitis; benign tumor; cancerous tumor; cancer; neoplasm; papilloma of choroid plexus; brain atrophy; dementia; schizophrenia; brain parenchyma loss; colloid cyst; atresia; normal pressure hydrocephalus (NPH); and ependymitis.

9. The method of claim 1, wherein the hydrocephalus is caused by at least one toxicity selected from the group consisting of: drug overdose; drug-drug interaction; poisoning; radiation; and idiopathic toxicity.

10. The method of claim 1, wherein the hydrocephalus is caused by at least one brain inflammation selected from the group consisting of: sepsis; allergy; and idiopathic inflammation.

11. A method to reduce at least one symptom of hydrocephalus in a patient in need thereof, the method comprising:
    a) administering a safe and effective amount of at least one Transient Receptor Potential Vanilloid Receptor 4 (TRPV4) antagonist, or a pharmaceutically-acceptable salt thereof, to the patient, wherein the at least one TRPV4 antagonist is RN-1734, HC-067047, or both RN-1734 and HC-067047; and
    b) slowing the progression of or ameliorating hydrocephalus in the patient.

12. The method of claim 11, wherein the at least one symptom of hydrocephalus is selected from the group consisting of: enlarged head circumference; failure of skull plates to fuse after third year in an infant; bulging, firm anterior and posterior fontanelles in an infant; retracted upper eyelids and downturned eyes; seizures; headache followed by vomiting; nausea; papilledema; blurred or double vision; sunsetting of the eyes; poor balance; poor coordination; gait disturbance; urinary incontinence; slowing or loss of developmental progress; lethargy; drowsiness; irritability; changes in personality or cognition including memory loss; impaired bladder control; incontinence; progressive mental impairment and dementia; progressive enlargement of the head; convulsion; tunnel vision; mental disability; Hakim's triad of gait instability; abducens nerve palsy; and vertical gaze palsy.

13. The method of claim 11, wherein the at least one symptom is diagnosed via a method selected from the group consisting of: ultrasound; computed tomography (CT) scan;

magnetic resonance imaging (MRI); radioisotope citernography; continuous intraventricular pressure recordings (over 24 hours or longer); and dynamic compliance studies.

14. The method of claim 11, wherein the patient is selected from the group consisting of: mouse; rat; guinea pig; cat; dog; monkey; horse; and human.

15. The method of claim 11, further comprising surgical placement of a cerebral spinal fluid (CSF) shunt in the patient.

\* \* \* \* \*